United States Patent
Simonini et al.

(12) 
(10) Patent No.: US 6,632,190 B2
(45) Date of Patent: Oct. 14, 2003

(54) INTRAOPERATIVE AUTOTRANSFUSION DEVICE

(75) Inventors: Giampaolo Simonini, Reggio Emilia (IT); Francesco Benatti, Concordia Sulla Secchia (IT)

(73) Assignee: Dideco S.p.A., Mirandola (IT)

( * ) Notice: Subject to any disclaimer, the term of this patent is extended or adjusted under 35 U.S.C. 154(b) by 43 days.

(21) Appl. No.: 09/819,004

(22) Filed: Mar. 27, 2001

(65) Prior Publication Data

US 2001/0044601 A1 Nov. 22, 2001

(30) Foreign Application Priority Data

Apr. 3, 2000 (IT) ...................................... MI2000A0702

(51) Int. Cl.[7] .............................................. A61M 37/00
(52) U.S. Cl. ..................... 604/5.01; 604/5.04; 604/6.15
(58) Field of Search ................................ 604/4.01, 5.01, 604/5.02, 5.03, 5.04, 6.01, 6.09, 6.11, 6.14, 6.19; 210/252, 253, 254, 255, 256, 645, 646, 647

(56) References Cited

U.S. PATENT DOCUMENTS

| 4,069,968 | A | | 1/1978 | Herman |
|---|---|---|---|---|
| 4,428,745 | A | | 1/1984 | Williams |
| 4,610,781 | A | | 9/1986 | Bilstad et al. |
| 4,653,719 | A | * | 3/1987 | Cabrera et al. ................. 251/7 |
| 4,668,214 | A | * | 5/1987 | Reeder .......................... 494/37 |
| 4,895,341 | A | * | 1/1990 | Brown et al. ................... 251/8 |
| 5,082,025 | A | | 1/1992 | DeVries et al. |
| 5,311,908 | A | | 5/1994 | Barone et al. |
| 5,769,385 | A | | 6/1998 | Burrous et al. |
| 5,891,080 | A | | 4/1999 | Skinkle et al. |

FOREIGN PATENT DOCUMENTS

WO    WO 98/22163    5/1998

* cited by examiner

*Primary Examiner*—Edward K. Look
*Assistant Examiner*—John K Fristor, Jr.
(74) *Attorney, Agent, or Firm*—Popovich & Wiles, P.A.

(57) ABSTRACT

An intraoperative autotransfusion system and method of use. The system includes an autotransfusion device, a removable cassette, a cardiotomy reservoir, a container for holding washing fluid, and a reservoir for containing processed blood. The removable cassette includes a centrifugal cell, a peristaltic pump, and multiple clamps, each having fixed and sliding elements. The cassette has a housing and multiple ducts for connection to the cardiotomy reservoir.

22 Claims, 8 Drawing Sheets

INTRAOPERATIVE AUTOTRANSFUSION DEVICE

FIELD OF THE INVENTION

The invention relates to an intraoperative autotransfusion device.

BACKGROUND OF THE INVENTION

It is known that the technique of intraoperative autotransfusion is becoming increasingly widespread. This technique allows a patient to be reinfused with the patient's own blood, recovered in the operating field during the procedure. The blood is recovered by using devices that comprise a blood collection cardiotomy reservoir, a centrifugal cell in which the red cells are concentrated and washed with a suitable solution, and a reinfusion pouch in which the washed and concentrated red cells are made available for reinfusion to the patient.

Known devices have less than fully satisfactory characteristics, and accordingly the aim of the present invention is to provide an intraoperative autotransfusion device which is easily managed by assigned operators and is highly reliable in operation.

SUMMARY OF THE INVENTION

The present invention provides an intraoperative autotransfusion device having a centrifugal cell, a peristaltic pump and first, second, and third clamps, each clamp having a fixed element and a sliding element, as well as first, second and third channels defined between their respective fixed and sliding elements. Each clamp includes a sliding element and a fixed element defining a channel therebetween. The first channel is configured to accommodate a first duct having a first lumen connected between the centrifugal cell and a source of unprocessed blood. The second channel is configured to accommodate a second duct connected between the centrifugal cell and a reservoir for holding processed blood. The third channel is configured to accommodate a third duct connected between the centrifugal cell and a washing liquid container. Each of the sliding elements are configured to move from a first position which impinges upon the duct to substantially close the lumen, to a second position which does not impinge upon the duct so the lumen is substantially open.

Also provided is a removable cassette that can be attached in an operational position on an intraoperative autotransfusion device having a centrifugal cell, a peristaltic pump and first, second, and third clamps, each clamp having a fixed element and a sliding element, as well as first, second and third channels defined between their respective fixed and sliding elements. The cassette includes a housing, first, second, and third ducts at least partially contained within the housing and each duct having a lumen. One end of the first duct is adapted for connection to a cardiotomy reservoir. One end of the second duct is adapted for connection to a container for holding washing liquid. One end of the third duct is adapted for connection to a reservoir for containing blood processed by the autotransfusion device. These ducts are secured within the housing at a location such that when the cassette is attached to the autotransfusion device in the operational position, the first, second and third ducts are positioned within the first, second and third channels, respectively. On the other ends of the ducts, a tube partially contained within the housing is fluidly connected. The tube's second end is adapted for connection to the centrifugal cell of the autotransfusion device.

In a further aspect of the invention, an intraoperative autotransfusion system is provided that comprises the autotransfusion device, the removable cassette, a cardiotomy reservoir for receiving blood from a patient, a container for holding washing fluid, and a reservoir for containing processed blood.

In yet another aspect of the invention, a method of using the intraoperative autotransfusion system is provided. A method of processing and re-infusing a patient's blood comprising: providing an intraoperative autotransfusion device which includes a centrifugal cell, a peristaltic pump and first, second, and third clamps, each clamp having a fixed element and a sliding element, defining first, second and third channels therebetween through the first, second and third clamps, respectively; providing a cassette including a housing, first, second, and third ducts at least partially contained within the housing, and a tube at least partially contained within the housing and fluidly connected to second ends of the first, second, and thirds ducts, the tube having an end adapted for connection to the centrifugal cell, a first end of the first duct being connected to a cardiotomy reservoir suitable for receiving blood from the patient, a first end of the second duct being connected to a container suitable for holding washing fluid; installing the cassette into the autotransfusion device such that the first, second and third ducts are positioned within the first, second and third channels, respectively; a first end of the third duct being connected to a reservoir suitable for containing processed blood; fitting the tube around a raceway of the peristaltic pump; connecting the tube to the centrifugal cell; operating the pump in a first direction; moving the first sliding element from a first position to a second position to allow blood to flow through the first duct from the cardiotomy reservoir into the cell; filling the centrifugal cell with blood; operating the centrifugal cell to concentrate the cells of the blood; moving the first sliding element from the second position to the first position to stop blood flow in the first duct; moving the second sliding element of the second duct from a first position to a second position to allow washing liquid to flow into the centrifugal cell to wash the blood; discontinuing the operation of the centrifugal cell; moving the second sliding element from the second position to the first position to stop blood flow in the second duct; operating the pump in a second direction; and moving the third sliding element of the third duct from a first position to a second position to allow washed blood to flow to the processed blood container for reinfusion to the patient.

BRIEF DESCRIPTION OF THE DRAWINGS

Further characteristics and advantages will become better apparent from the description of a preferred but not exclusive embodiment of the invention, illustrated only by way of non-limitative example in the accompanying drawings, wherein.

DETAILED DESCRIPTION OF THE PREFERRED EMBODIMENTS

Referring now to the figures, cardiotomy reservoir 1 receives blood from the operating field, pouch 2 contains concentrated washed blood for reinfusion to the patient, and container 3 contains washing liquid. Reservoir 1, pouch 2 and container 3 are connected by ducts 4, 5 and 6, respectively, to cassette 7.

Figure 1:
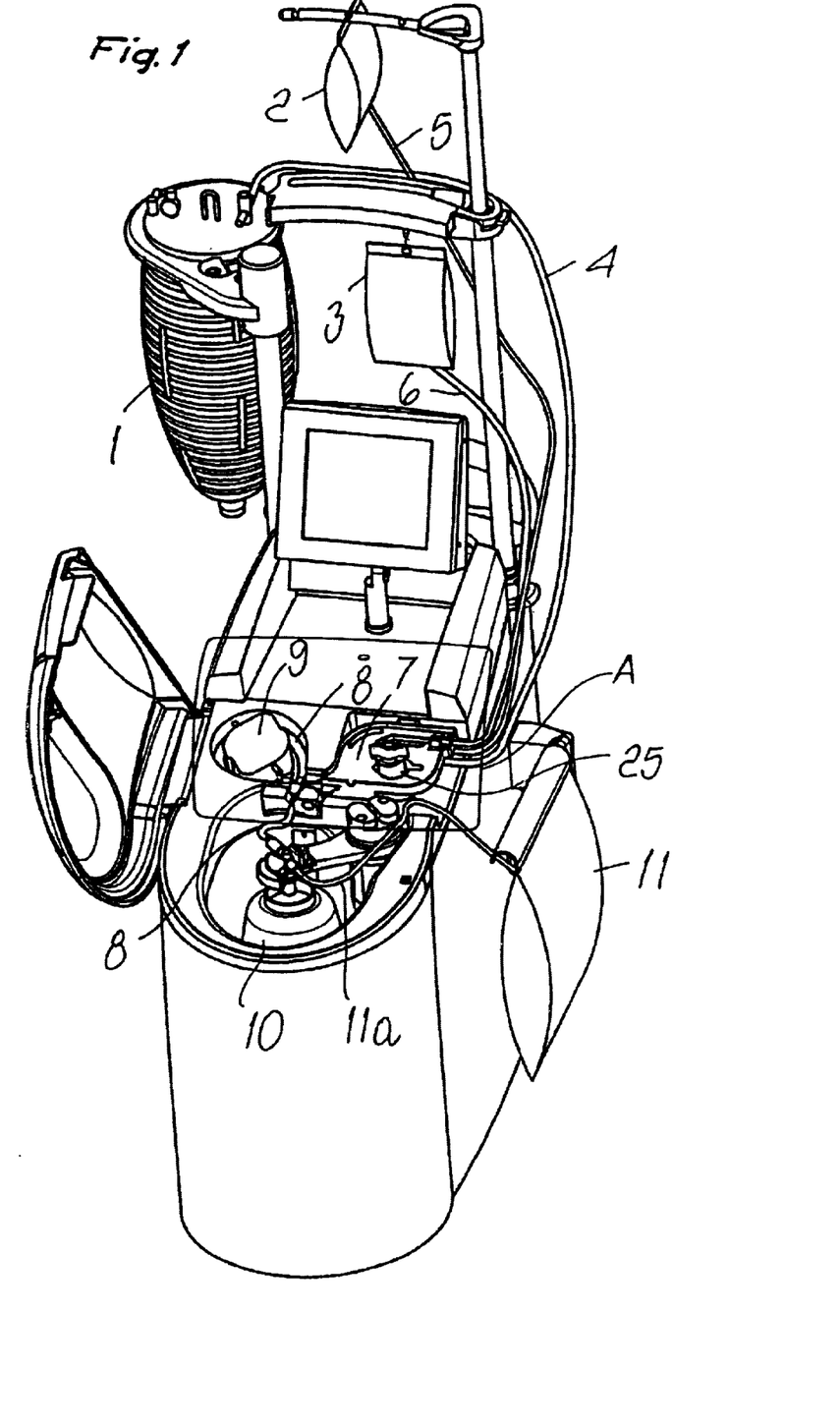
FIG. 1 is a perspective view of a preferred embodiment of the invention.
Figure 2:
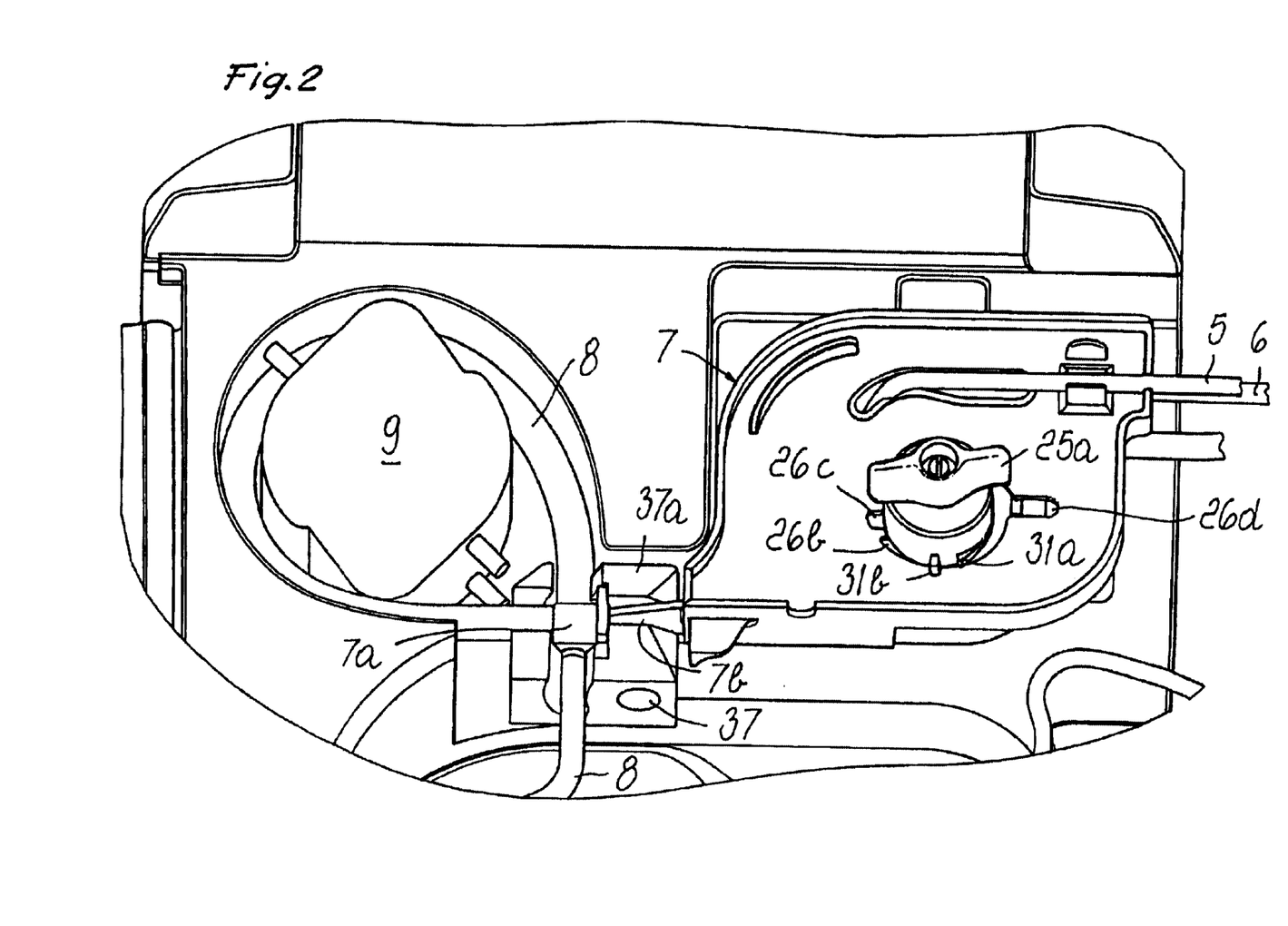
FIG. 2 is a blown up view of detail "A" of FIG. 1.
Figure 3:
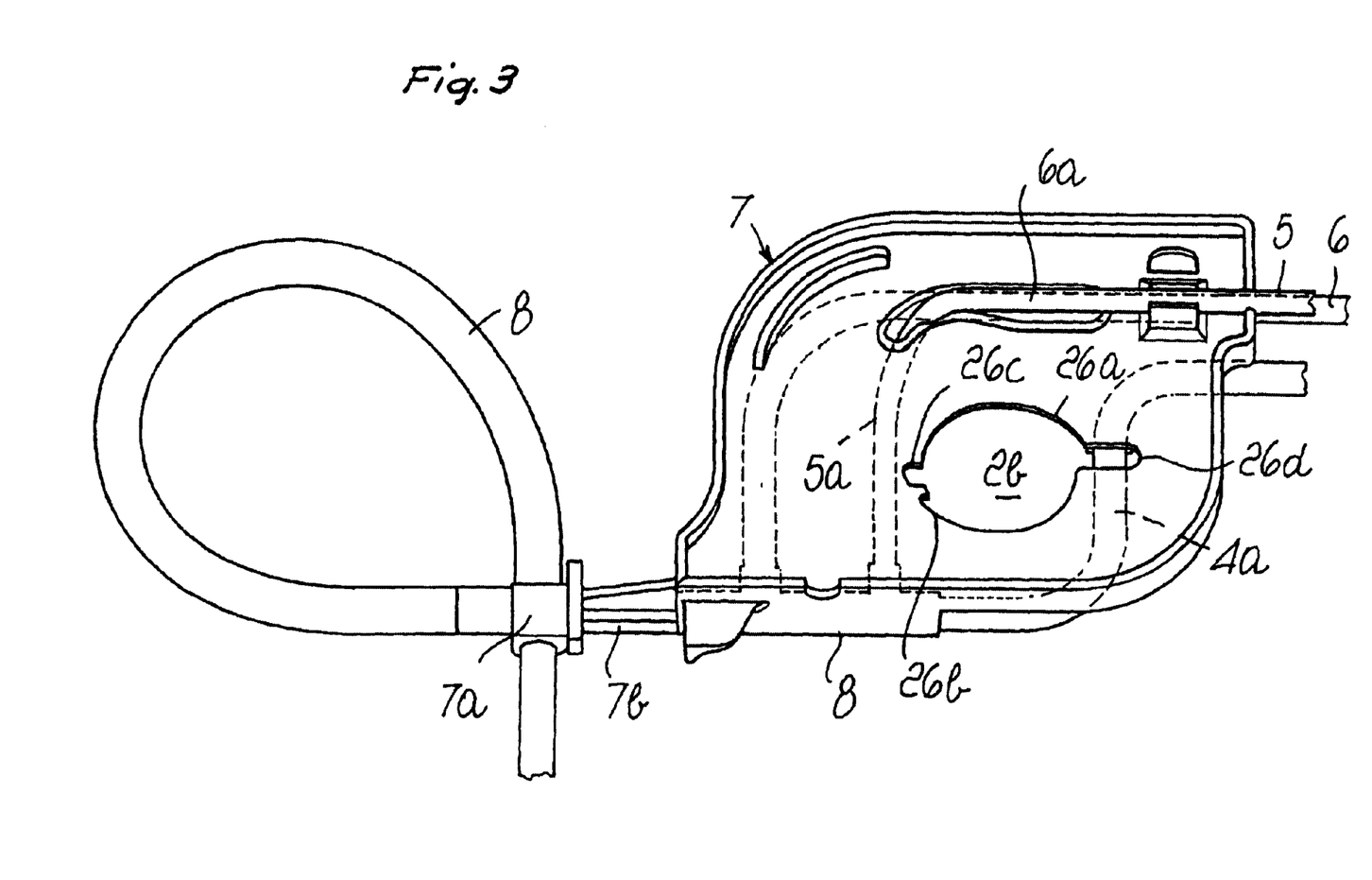
FIG. 3 is a front view of a preferred embodiment of a cassette.
Figure 4:
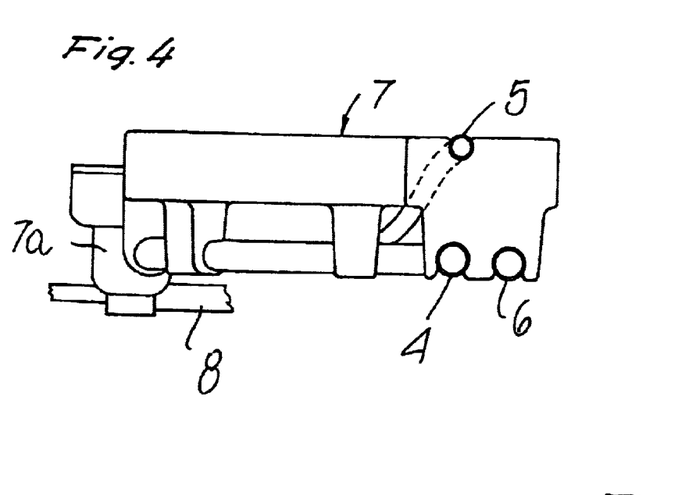
FIG. 4 is a side view of a preferred embodiment of a cassette.

Within cassette 7, ducts 4, 5 and 6 are connected, as shown in particular in FIG. 3, to a single tube 8, of which a portion is preferably noose-shaped by virtue of the particular shape of the end 7a of a tab 7b of cassette 7, as best seen in FIGS. 1 and 2. Tube 8 is inserted in peristaltic pump 9 and extends to centrifugal cell 10, which is meant to be turned by conventional means not shown in the figure. A duct 11a for connection to a waste pouch 11 leads out from centrifugal cell 10.

Again referring to FIG. 3, end portions 4a, 5a, and 6a of the ducts 4, 5 and 6, respectively, before coupling to the tube 8, are accommodated in the cassette 7 so that they are co-planar. When cassette 7 is inserted in an autotransfusion device (as shown in FIGS. 1 and 2), the portions 4a, 5a and 6a lie within three channels designated by the reference numerals 12, 13 and 14, respectively, as shown in FIG. 5, with insertion criteria described hereinafter.

The channel 12 is provided with a clamp which comprises movable sliding element 15. Sliding element 15 is preferably kept in a closed position, as shown in FIGS. 5 and 6, where ridge 15a can be held against fixed element 16, by the action of springs 17a, 17b as best seen in FIGS. 6 and 7.

Figure 5:
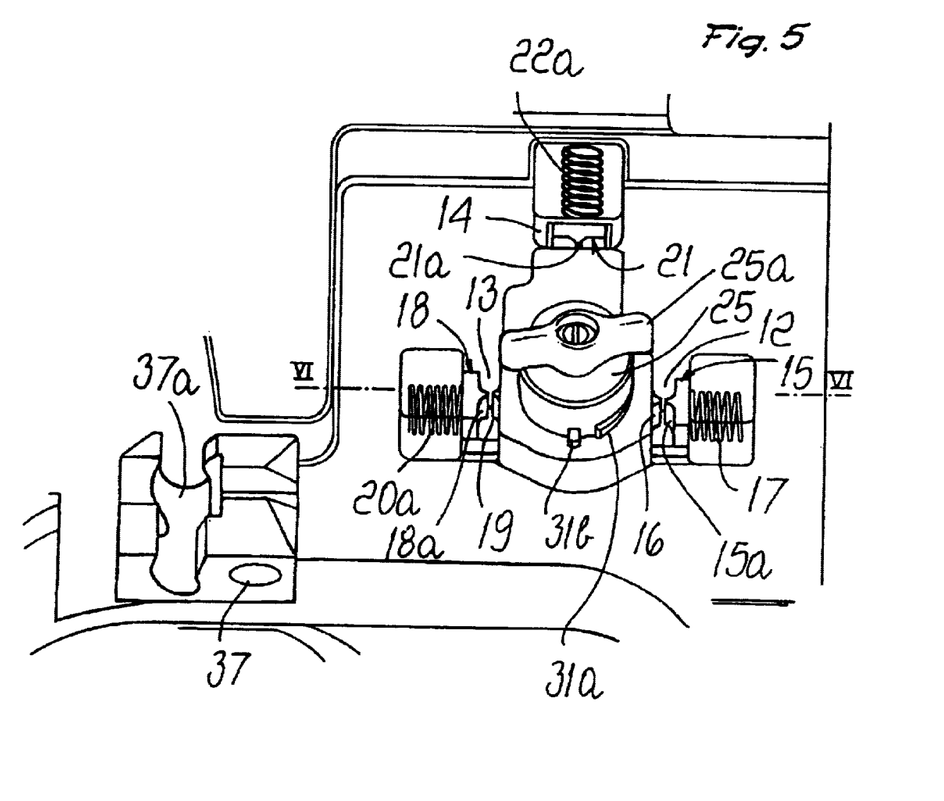
FIG. 5 is a blown up view of a portion of the device.
Figure 6:
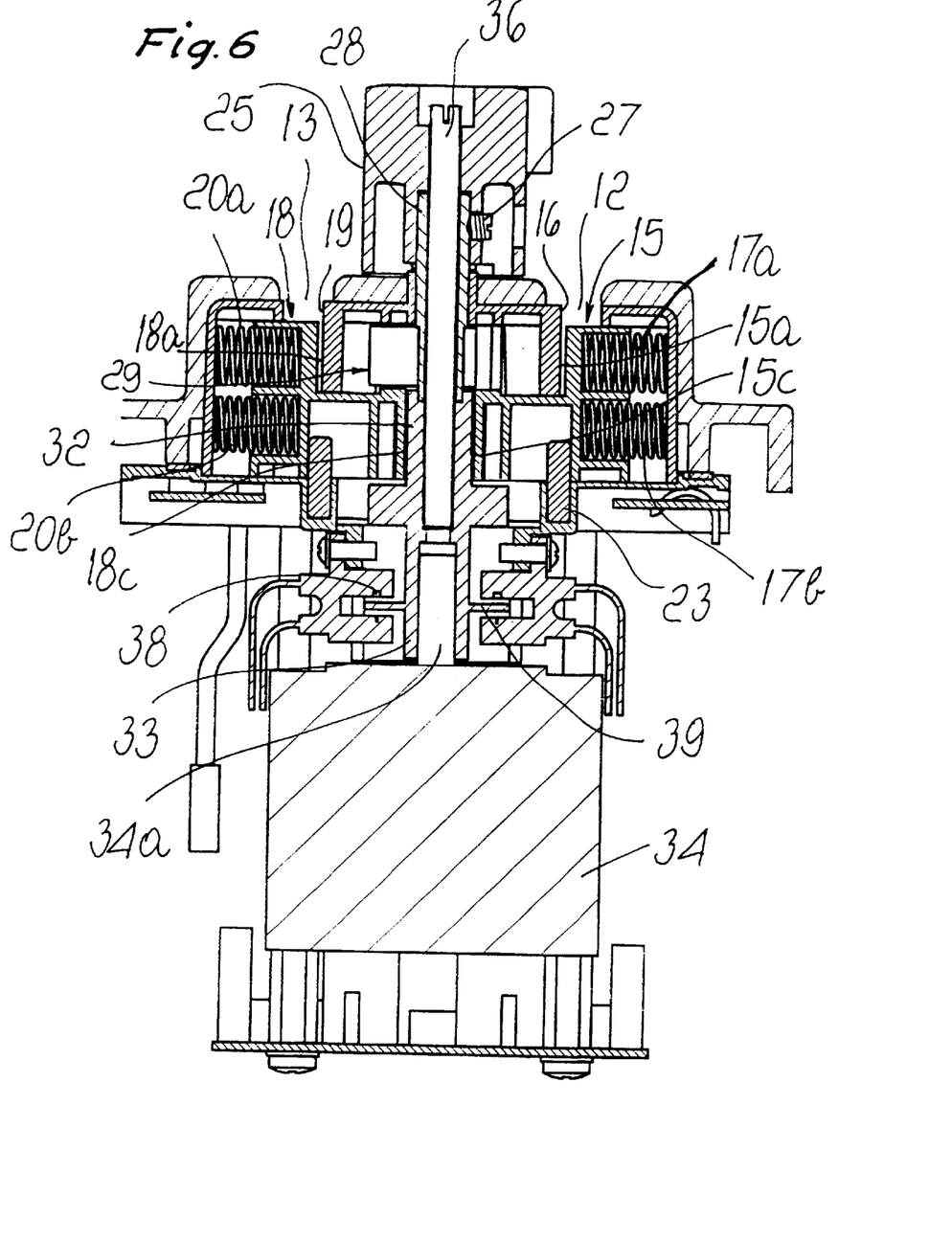
FIG. 6 is a sectional view, taken along line 6—6 of FIG. 5.
Figure 7:
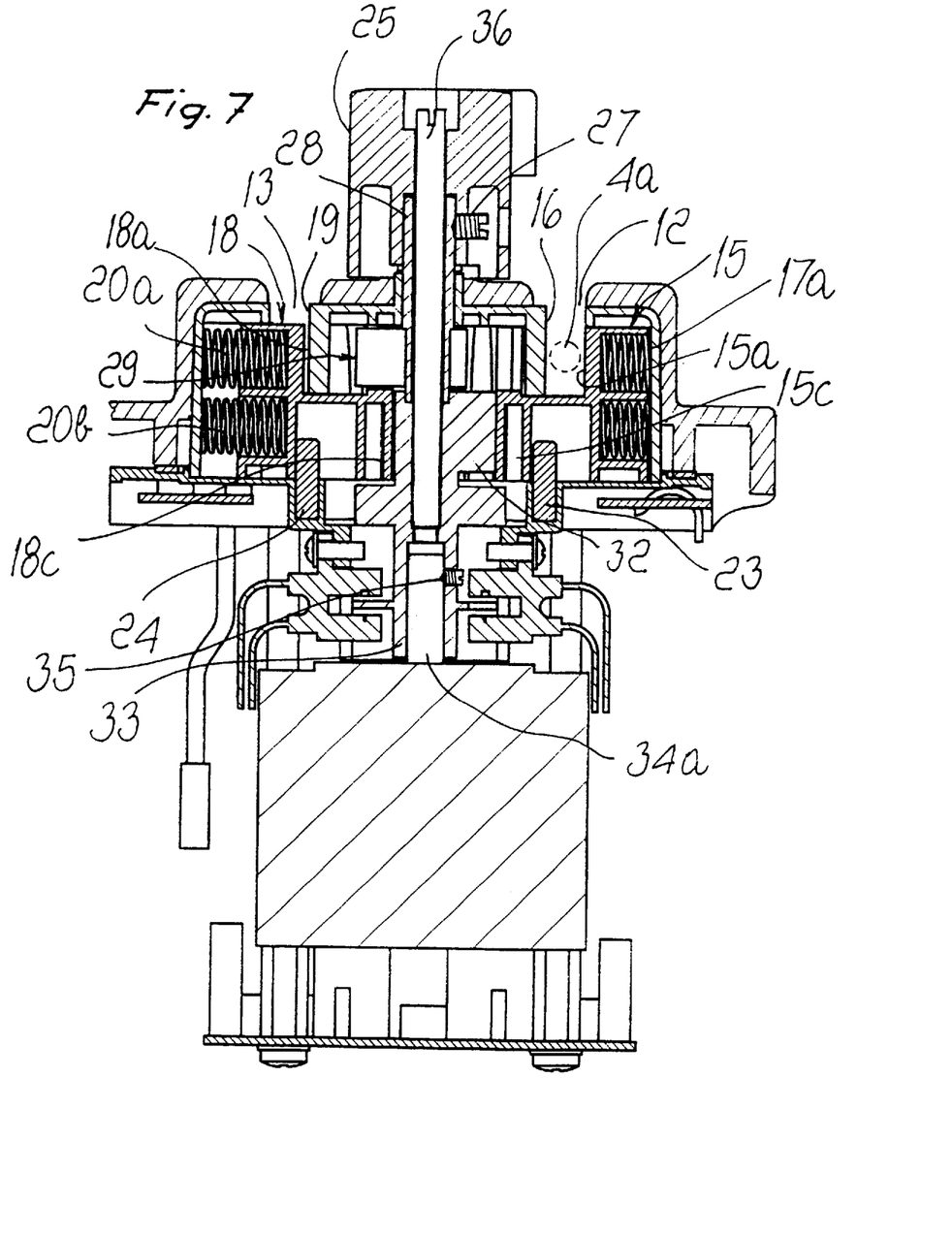
FIG. 7 is a sectional view, taken along line 6—6 of FIG. 5, in a different step of operation than in FIG. 6.
Figure 8:
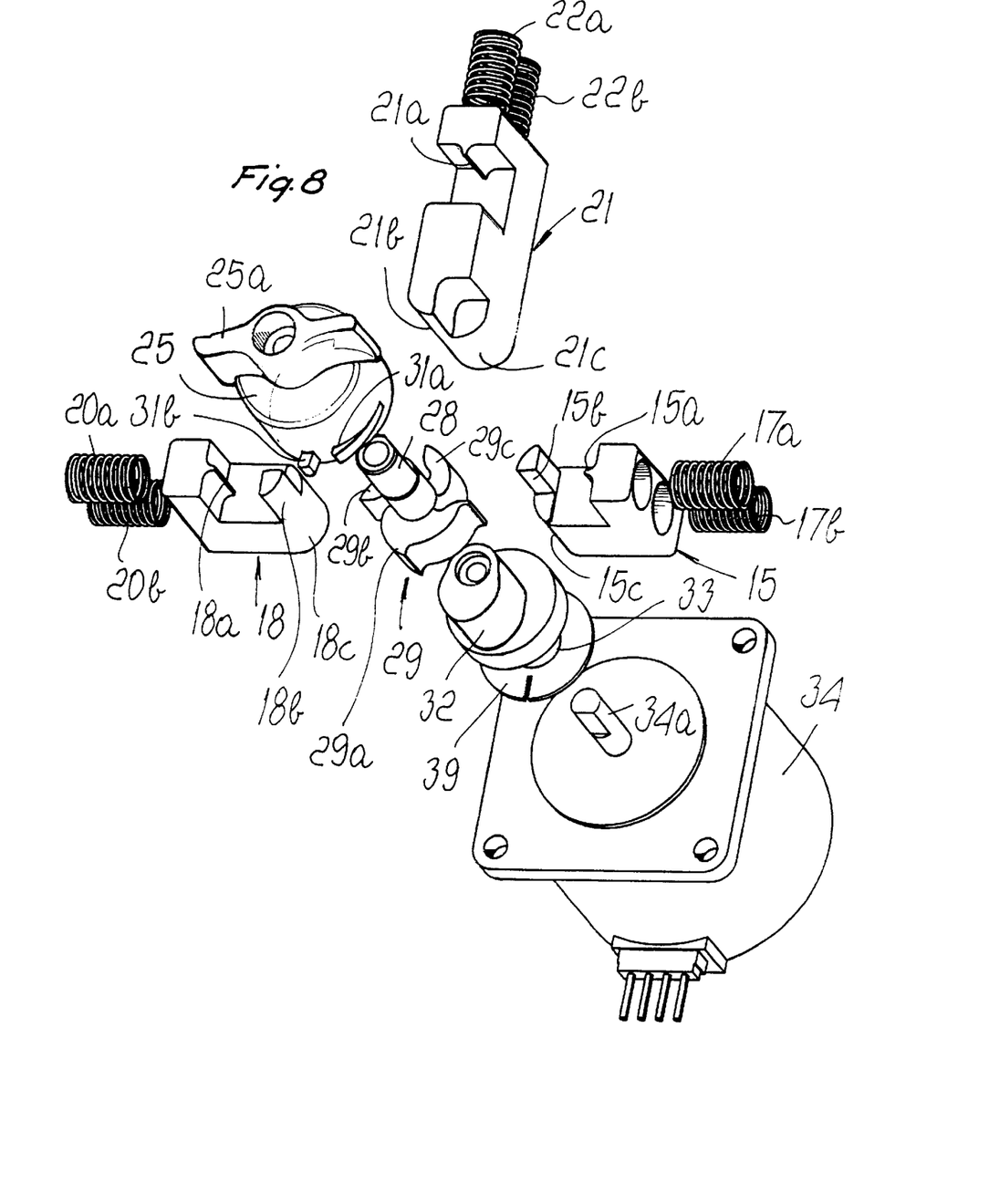
FIG. 8 is an exploded view of a motor assembly of the invention.

Likewise, channel 13 is provided with a clamp which comprises a movable sliding element 18 that is preferably kept in a closed position, as shown in FIGS. 5, 6 and 7. In this closed position, ridge 18a preferably rests against fixed element 19, by virtue of the action of springs 20a and 20b. Channel 14 is provided with a clamp comprising a movable sliding element 21 with a ridge 21a which is preferably kept in a closed position by the action of springs 22a, 22b as seen in FIG. 8.

Fixed safety pins, such as pin 23 for sliding element 15 and pin 24 for sliding element 18, are provided to limit the movement of the sliding elements in both directions.

Knob 25 is preferably operated manually by gripping handle 25a. Knob 25 passes through cassette 7 within an opening 26 provided therein, and is connected by a grub screw 27 to a pivot 28, which is monolithically coupled to a triple cam 29. As seen in FIG. 8, cam 29 comprises elements 29a, 29b, 29c, which make contact preferably with sliding element portions 15b, 18b, 21b, respectively, for simultaneous actuation in a direction opposite the action of the previously mentioned springs.

The knob 25 is provided with a lock for securing cassette 7 when it is inserted in the device. The lock may comprise a gradually sloping tooth 30. Tooth 30 is preferably shaped complementarily with respect to notch 26a provided at the rim of opening 26 of the cassette 7. A second tooth formed by portions 31a and 31b, which is shaped complementarily with respect to the notch which is formed by the two portions 26b, 26c is provided at the rim of the opening 26. At the rim of opening 26 there is also a notch 26d, which allows easy passage of handle 25a with a wide clearance.

As seen in FIGS. 6 and 7, a motorized cam 32 can be monolithically connected to the pivot 33. Pivot 33 is associated with an output shaft 34a of an electric motor 34 and can be locked thereon by virtue of a grub screw 35.

Cam 32 is preferably inserted in the device coaxially to pivot 28 of triple cam 29 that rests thereon so that it is centered and can rotate freely. Cam 32 is suitable to make contact with one sliding element at a time, according to an operating logic of the device described hereinafter, at the portions 15c, 18c, 21c of the sliders to cause them to move in contrast with the action of the springs.

A rod 36, which is coaxial to the pivots 28 and 33, passes inside them and is rigidly coupled, at its lower end, to pivot 33 for the manual actuation of motorized cam 32 if electric motor 34 fails to operate.

Referring again to FIG. 2, a hematocrit sensor 37 comprised within block 37a can be provided for accommodating terminal 7a and the corresponding tab 7b of the cassette 7. Referring to FIG. 6, optical sensors 38 working in combination with phonic wheel 39 on pivot 33 can detect the position of the motorized cam. Optionally, additional sensors can be provided within the device if desired.

Figure 9:
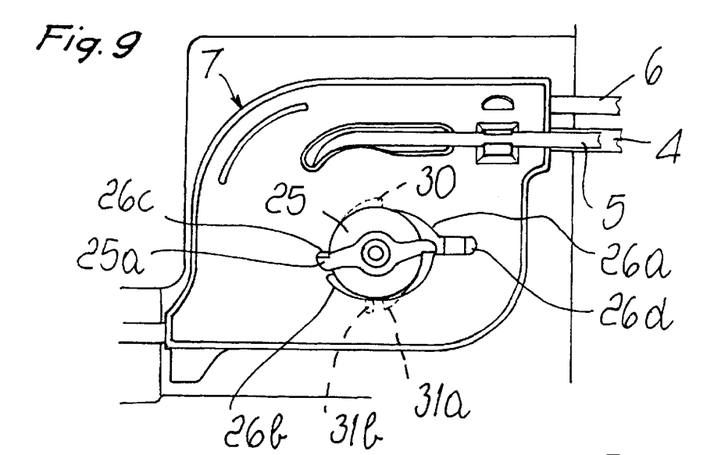
FIGS. 9, 10 and 11 are views of three steps of the insertion of a supporting cassette in a preferred embodiment of the device.

The operation of the invention generally begins with the insertion of cassette 7 in the device (shown in FIGS. 5 and 6) with knob 25 at its first stroke limit and cam 32 in a neutral position, so as to not actuate any sliding elements. Cassette 7 is positioned so that the opening 26 lies at knob 25, accommodating terminal 7a with tab 7b in the block 37a. Tube 8 is then connected to centrifugal cell 10 and inserted in the peristaltic pump 9. Cassette 7 preferably is prohibited from moving downward by having the sliding elements 15, 18, 21 in their closed positions, so as to prevent the passage of the ducts, and also by having teeth 30 and 31a, 31b interfere with the plane of the cassette. This condition is shown in FIG. 9.

Figure 10:
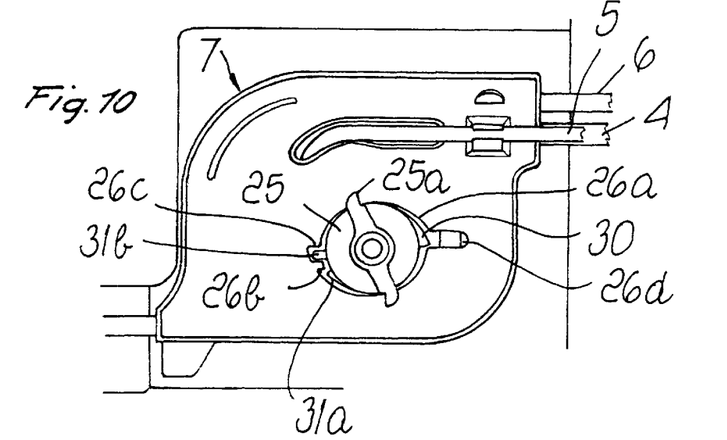

Knob 25 is then turned to bring it to its second stroke limit as shown in FIG. 10, keeping it motionless in the position that it has reached in order to overcome the action of the springs that act on the sliding elements 15, 18 and 21 in contact with the triple cam 29 connected thereto. This results in the dual effect of simultaneously moving the sliding elements, by virtue of the action of the triple cam, into the open position, and of arranging the teeth 30 and 31a, 31b, at the notches 26a and 26b, 26c, respectively, provided at the rim of the opening 26 of the cassette.

Cassette 7 can then be moved downward to a working position by inserting the duct portions 4a, 5a and 6a respectively in channels 12, 13, 14. Correctness of the operation can be ensured by the presence of the reference tooth 31b inserted in the corresponding notch 26c.

Figure 11:
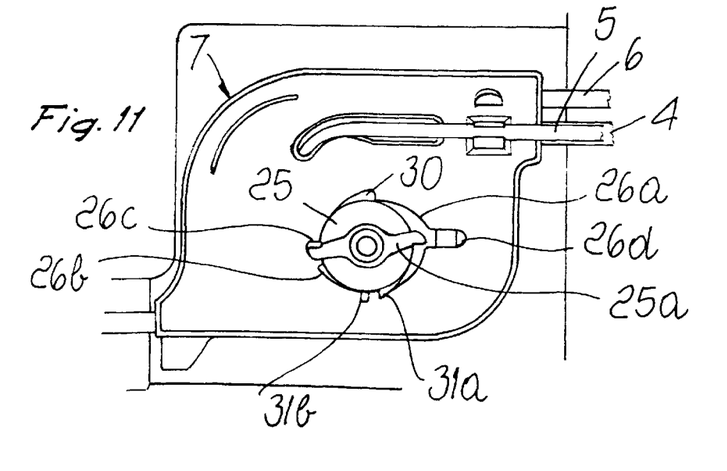

When knob 25 is released, and by virtue of the thrust applied by sliding elements 15, 18 and 21 due to the action of the corresponding springs against triple cam 29, the knob returns to the initial position, as shown in FIG. 11, with the cassette 7 locked by teeth 30 and 31a, 31b and with the duct portions 4a, 5a, 6a closed by the respective clamps. This is the position shown in FIGS. 1, 2, 5, 6, 8 and 11.

After starting the rotation of centrifugal cell 10 and starting peristaltic pump 9, the controller of the device activates electric motor 34 which moves cam 32 from the neutral position, shown in FIGS. 6 and 8, to the position shown in FIG. 7, with a movement of sliding element 15 which produces the opening of the portion 4a, as shown in the FIG. 7, of the duct 4 that arrives from the cardiotomy reservoir 1. Blood can thus flow from cardiotomy reservoir 1 into centrifugal cell 10, and the step for filling the cell and concentrating the red cells can be performed. Upon completion of filling and concentrating, the motor is caused to turn cam 32 to close sliding element 15 and actuate sliding element 21 to open portion 6a of duct 6 that arrives from the washing liquid container 3. This opens duct 6 to allow washing liquid to flow into centrifugal cell 10. The centrifugal cell 10 and peristaltic pump 9 continue to turn and the step for washing the concentrated red cells is completed. The waste is sent to pouch 11.

Once washing has been completed, cell 10 stops, cam 32 is caused to rotate to actuate sliding element 18. This results in the closure of duct portion 6a and the opening of portion 5a of duct 5 which is connected to the pouch 2. The peristaltic pump 9 then reverses the direction of its rotation and sends the concentrated and cleaned blood to the pouch 2 for reinfusion to the patient. The process is thus complete, and cassette 7 can then be released by actuating the knob 25.

The described invention is susceptible of numerous modifications and variations, all of which are within the scope of the appended claims; all the details may furthermore be replaced with other technically equivalent elements.

What is claimed is:

1. A cassette configured for removable attachment in an operational position on an intraoperative autotransfusion device, which includes a centrifugal cell, a peristaltic pump and first, second, and third clamps, each clamp having a fixed element and a sliding element, the first, second and third clamps having first, second and third channels respectively, defined between their respective fixed and sliding elements, the cassette comprising:
 a housing;
 first, second, and third ducts at least partially contained within the housing, the first, second and third ducts having first, second, and third lumens respectively, each duct having a first end and a second end, the first end of the first duct being adapted for connection to a cardiotomy reservoir, the first end of the second duct being adapted for connection to a container for holding washing liquid, the first end of the third duct being adapted for connection to a reservoir for containing blood processed by the autotransfusion device, the first, second and third ducts being secured within the housing at a location such that when the cassette is attached to the autotransfusion device in the operational position, the first, second and third ducts are positioned within the first, second and third channels, respectively; and
 a tube at least partially contained within the housing and fluidly connected to the second ends of the first, second, and thirds ducts, the tube having an end adapted for connection to the centrifugal cell.

2. The cassette according to claim 1 wherein the portions of first, second and third ducts contained within the housing are co-planar.

3. The cassette according to claim 1 wherein a portion of the tube is looped and sized to fit around a raceway of the peristaltic pump.

4. An autotransfusion system comprising:
 (i) a an autotransfusion device comprising:
 a centrifugal cell;
 a pump for causing fluid flow into and out of the centrifugal cell; and
 first, second and third clamps, each clamp including a sliding element and a fixed element defining a channel therebetween, including first, second and third channels through the first, second, and third clamps, respectively; and
 (ii) a cassette configured for removable attachment in an operational position on the autotransfusion device,
 the cassette comprising:
 a housing;
 first, second, and third ducts at least paritally contained within the housing, the first, second and third ducts having first, second, and third lumens respectively, each duct having a first end and a second end, the first end of the first duct being adapted for connection to a cardiotomy reservoir, the first end of the second duct being adapted for connection to a container for holding washing liquid, the first end of the third duct being adapted for connection to a reservoir for containing blood processed by the autotransfusion device, the first, second and third ducts being secured within the housing at a location such that when the cassette is attached to the autotransfusion device in the operational position, the first, second and third ducts are positioned within the first, second and third channels, respectively; and
 a tube at least partially contained within the housing and fluidly connected to the second ends of the first, second and third ducts, the tube having an end adapted for connection to the centrifugal cell.

5. The system according to claim 4 wherein the autotransfusion device further comprises movement-limiting elements to limit the movement of the sliding elements.

6. The system according to claim 4 wherein the autotransfusion device further comprises a cam, the cam having a first portion including a plurality of extending members adapted to simultaneously contact and move the first, second and third sliding elements from the first position to the second position when the cam is rotated to a first position.

7. The system according to claim 6 wherein the cam has a second portion having an oblong shape adapted to selectively and individually contact the first, second and third sliding elements upon rotation of the cam.

8. The system according to claim 6 wherein the autotransfusion device further comprises a knob coaxially positioned with respect to the cam, the knob being connected for manually turning the cam.

9. The system according to claim 4 wherein the autotransfusion device further comprises a control member configured for automatically moving at least one sliding element at a time from a first position to a second position.

10. An intraoperative autotransfusion system comprising:
 a cardiotomy reservoir suitable for receiving blood from a patient;
 a container suitable for holding blood washing fluid;
 a reservoir suitable for containing processed blood;
 an autotransfusion device including a centrifugal cell, a pump, and first, second, and third clamps, each clamp having a fixed element and a sliding element, defining first, second and third channels therebetween through the first, second and third clamps, respectively; and
 a cassette configured for removable attachment in an operational position on the autotransfusion device, the cassette comprising:
 a housing;
 first, second, and third ducts at least partially contained within the housing, the first, second and third ducts having first, second, and third lumens respectively, each duct having a first end and a second end, the first end of the first duct being adapted for connection to the cardiotomy reservoir, the first end of the second duct being adapted for connection to the container for holding washing liquid, the first end of the third duct being adapted for connection to the reservoir for containing blood processed by the autotransfusion device, the first, second and third ducts being secured within the housing at a location such that when the cassette is attached to the autotransfusion device in the operative position, the first, second and third ducts are positioned within the first, second and third channels, respectively; and a tube at least partially contained within the housing and fluidly connected to the second ends of the first, second, and thirds ducts, the tube having an end adapted for connection to the centrifugal cell.

11. The system according to claim 10 wherein a portion of the tube is looped and sized to fit within a raceway of the pump.

12. The system according to claim 10 wherein the pump is connected to cause bidirectional flow through the tube.

13. The system according to claim 10 further comprising movement-limiting elements to limit the movement of the sliding elements.

14. The system according to claim 10 further comprising a hematocrit sensor contained within the housing.

15. The system according to claim 10 wherein the autotransfusion device further comprises a cam, the cam having a first portion including a plurality of extending members adapted to simultaneously contact and move the first, second and third sliding elements from the first position to the second position when the cam is rotated to a first position.

16. The system according to claim 15 wherein the cam has a second portion having an oblong shape adapted to selectively and individually contacting the first, second and third sliding elements upon rotation of the cam.

17. The system according to claim 15 wherein the autotransfusion device further comprises a knob coaxially positioned with respect to the cam, the knob being connected for manually turning the cam.

18. The system according to claim 15 wherein the autotransfusion device further comprises a control member configured to automatically actuate the cam.

19. The system according to claim 15 further including a motor connected to rotate the cam.

20. The system according to claim 15 further comprising at least one optical sensor to detect the position of the cam.

21. A method of processing and re-infusing a patient's blood comprising:

providing an intraoperative autotransfusion device which includes a centrifugal cell, a peristaltic pump and first, second, and third clamps, each clamp having a fixed element and a sliding element, defining first, second and third channels therebetween through the first, second and third clamps, respectively;

providing a cassette including a housing, first, second, and third ducts at least partially contained within the housing, and a tube at least partially contained within the housing and fluidly connected to second ends of the first, second, and thirds ducts, the tube having an end adapted for connection to the centrifugal cell, a first end of the first duct being connected to a cardiotomy reservoir suitable for receiving blood from the patient, a first end of the second duct being connected to a container suitable for holding washing fluid;

installing the cassette into the autotransfusion device such that the first, second and third ducts are positioned within the first, second and third channels, respectively;

a first end of the third duct being connected to a reservoir suitable for containing processed blood;

fitting the tube around a raceway of the peristaltic pump;

connecting the tube to the centrifugal cell;

operating the pump in a first direction;

moving the first sliding element from a first position to a second position to allow blood to flow through the first duct from the cardiotomy reservoir into the cell;

filling the centrifugal cell with blood;

operating the centrifugal cell to concentrate the cells of the blood;

moving the first sliding element from the second position to the first position to stop blood flow in the first duct;

moving the second sliding element of the second duct from a first position to a second position to allow washing liquid to flow into the centrifugal cell to wash the blood;

discontinuing the operation of the centrifugal cell;

moving the second sliding element from the second position to the first position to stop blood flow in the second duct;

operating the pump in a second direction; and moving the third sliding element of the third duct from a first position to a second position to allow washed blood to flow to the processed blood container for reinfusion to the patient.

22. The method according to claim 21 further comprising the step of sending waste to a waste pouch.

* * * * *